(12) United States Patent
Dahl

(10) Patent No.: US 7,258,060 B2
(45) Date of Patent: Aug. 21, 2007

(54) PISTON AND SCRAPER ASSEMBLY

(75) Inventor: Peder Dahl, Gentofte (DK)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 10/541,286

(22) PCT Filed: Dec. 29, 2003

(86) PCT No.: PCT/EP03/14946

§ 371 (c)(1),
(2), (4) Date: Mar. 6, 2006

(87) PCT Pub. No.: WO2004/059314

PCT Pub. Date: Jul. 15, 2004

(65) Prior Publication Data

US 2006/0156918 A1 Jul. 20, 2006

(30) Foreign Application Priority Data

Dec. 30, 2002 (GB) .................................. 0230265.1

(51) Int. Cl.
*G01N 30/60* (2006.01)
*F16J 1/00* (2006.01)
(52) U.S. Cl. .................... 92/194; 92/255; 210/198.2
(58) Field of Classification Search .................. 92/194, 92/203, 255; 210/198.2
See application file for complete search history.

(56) References Cited

U.S. PATENT DOCUMENTS

| | | | |
|---|---|---|---|
| 2,814,540 A | 11/1957 | Southerwick | |
| 3,747,479 A * | 7/1973 | Nightingale et al. | 92/203 |
| 3,966,609 A * | 6/1976 | Godbille et al. | 210/198.2 |
| 4,804,290 A | 2/1989 | Balsells | |
| 4,889,351 A | 12/1989 | Frost | |
| 4,891,133 A | 1/1990 | Colvin, Jr. | |
| 5,113,747 A | 5/1992 | Pignerol | |
| 5,169,522 A * | 12/1992 | Shalon et al. | 210/198.2 |
| 5,192,433 A | 3/1993 | Shalon | |
| 5,378,361 A * | 1/1995 | Baeckstrum | 210/198.2 |
| 5,423,982 A | 6/1995 | Jungbauer et al. | |
| 5,693,223 A * | 12/1997 | Yamada et al. | 210/198.2 |
| 6,802,968 B2 * | 10/2004 | Leavesley et al. | 210/198.2 |
| 6,923,908 B1 * | 8/2005 | Thompson et al. | 210/198.2 |
| 6,932,904 B2 * | 8/2005 | Laub et al. | 210/198.2 |

FOREIGN PATENT DOCUMENTS

| | | |
|---|---|---|
| EP | 0 476 996 | 3/1992 |
| GB | 646249 | 11/1950 |

* cited by examiner

*Primary Examiner*—Thomas E. Lazo
(74) *Attorney, Agent, or Firm*—Dwayne L. Bentley; Yonggang Ji

(57) ABSTRACT

A piston and scraper assembly (26) for a high-pressure liquid chromatography column (1) is provided with a snap lock between the piston (5) and the scraper (25). The snap lock comprises a groove (23) in the piston wall (17), a complementary groove (39) in the inner face of the scraper (25) and a locking, sealing and biasing means such as a resilient O-ring (43) which fits into said grooves.

5 Claims, 3 Drawing Sheets

PISTON AND SCRAPER ASSEMBLY

CROSS REFERENCE TO RELATED APPLICATIONS

This application is a filing under 35 U.S.C. § 371 and claims priority to international patent application number PCT/EP2003/014946 filed Dec. 29, 2003, published on Jul. 15, 2004 as WO 2004/059314 and also claims priority to patent application number 0230265.1 filed in Great Britain on Dec. 30, 2002; the disclosures of which are incorporated herein by reference in their entireties.

FIELD OF THE INVENTION

The present invention relates to piston and scraper assemblies, for high-pressure chromatography columns, of the type mentioned in the preambles of the independent claims.

PRIOR ART

In high-pressure chromatographic columns, a piston is often arranged movably in the chromatography column in order to allow the chromatography medium to be compressed and consolidated by the piston. In this way a substantially homogeneous bed of separation medium can be obtained. A problem which occurs during compression of the medium is that abrasive medium particles can become trapped between the sides of the piston and the column wall. These particles not only damage the cylinder walls but can also damage the piston seals. U.S. Pat. No. 5,169,522 describes a high pressure chromatography column with a piston movable in the chromatography cylinder in which the head of the piston is provided with a frit holder which supports a cylinder wall scraper. The purpose of the scraper is to move packing media ahead of the piston in order to prevent the packing media from reaching the sealing O-rings on the piston wall. The scraper is in the form of a ring with an internal thread with co-operates with a externally threaded portion of the frit holder. A problem with this prior art device is that in order to prevent packing media from passing the scraper, the gap between the scraper and the cylinder wall must be smaller than the diameter of media particles. This requires very fine, and expensive, machining tolerances and surface finishes on both the scraper and the cylinder wall. Additionally, the scraper is unable to prevent the liquid from coming into contact with the sealing O-rings on the piston wall. This is a problem if the O-rings are not resistant to the liquids used in the column, such as cleaning liquids or process liquids.

SUMMARY OF THE INVENTION

According to the present invention, at least some of the problems with the prior art are solved by means of a piston and scraper assembly having the features present in the characterizing part of claim 1.

DETAILED DESCRIPTION OF EMBODIMENTS ILLUSTRATING THE INVENTION

Figure 1:
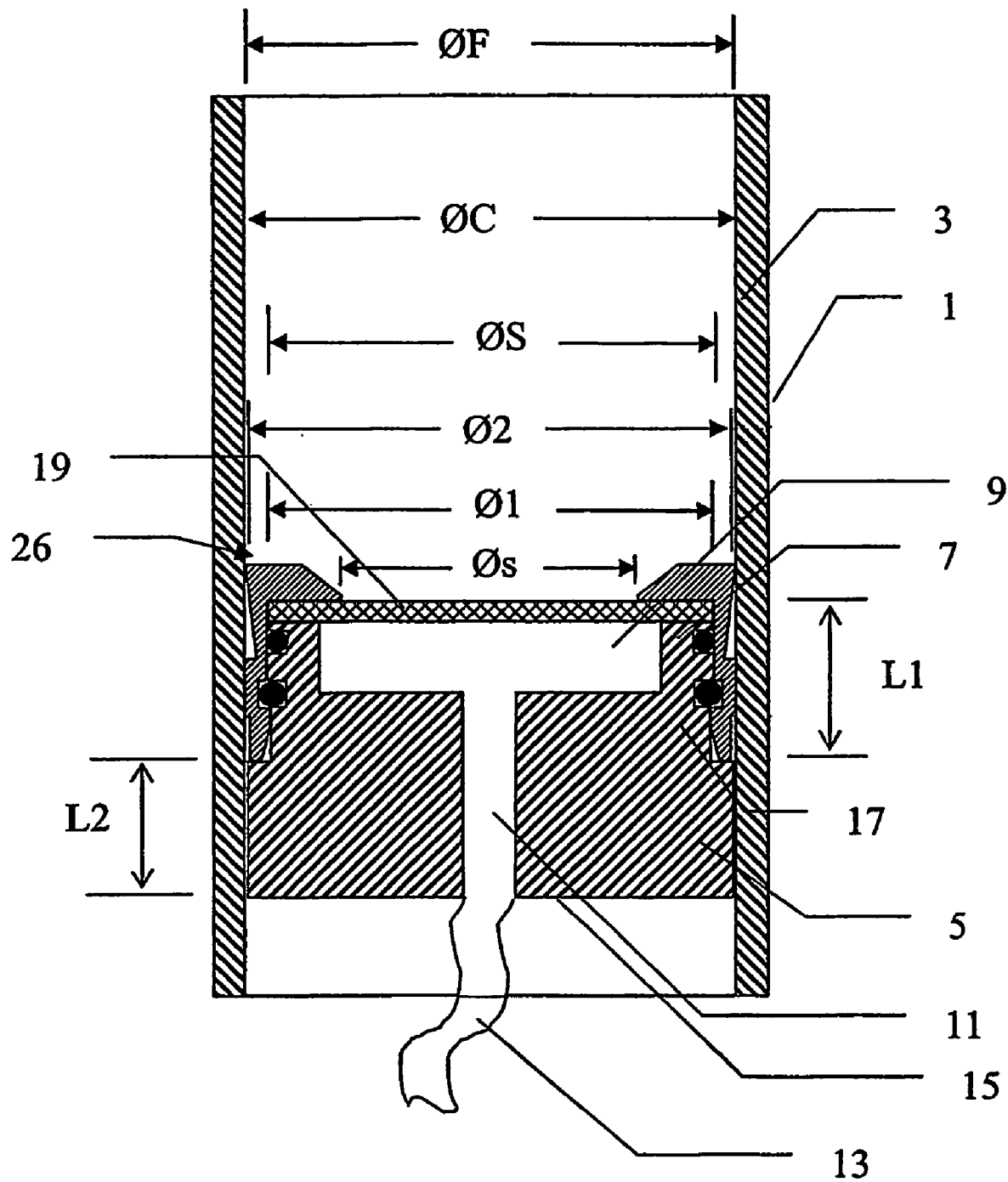
FIG. 1 shows a schematically cross-section though a portion of a chromatography column provided with a piston and scraper assembly in accordance with a first embodiment of the present invention.
Figure 2:
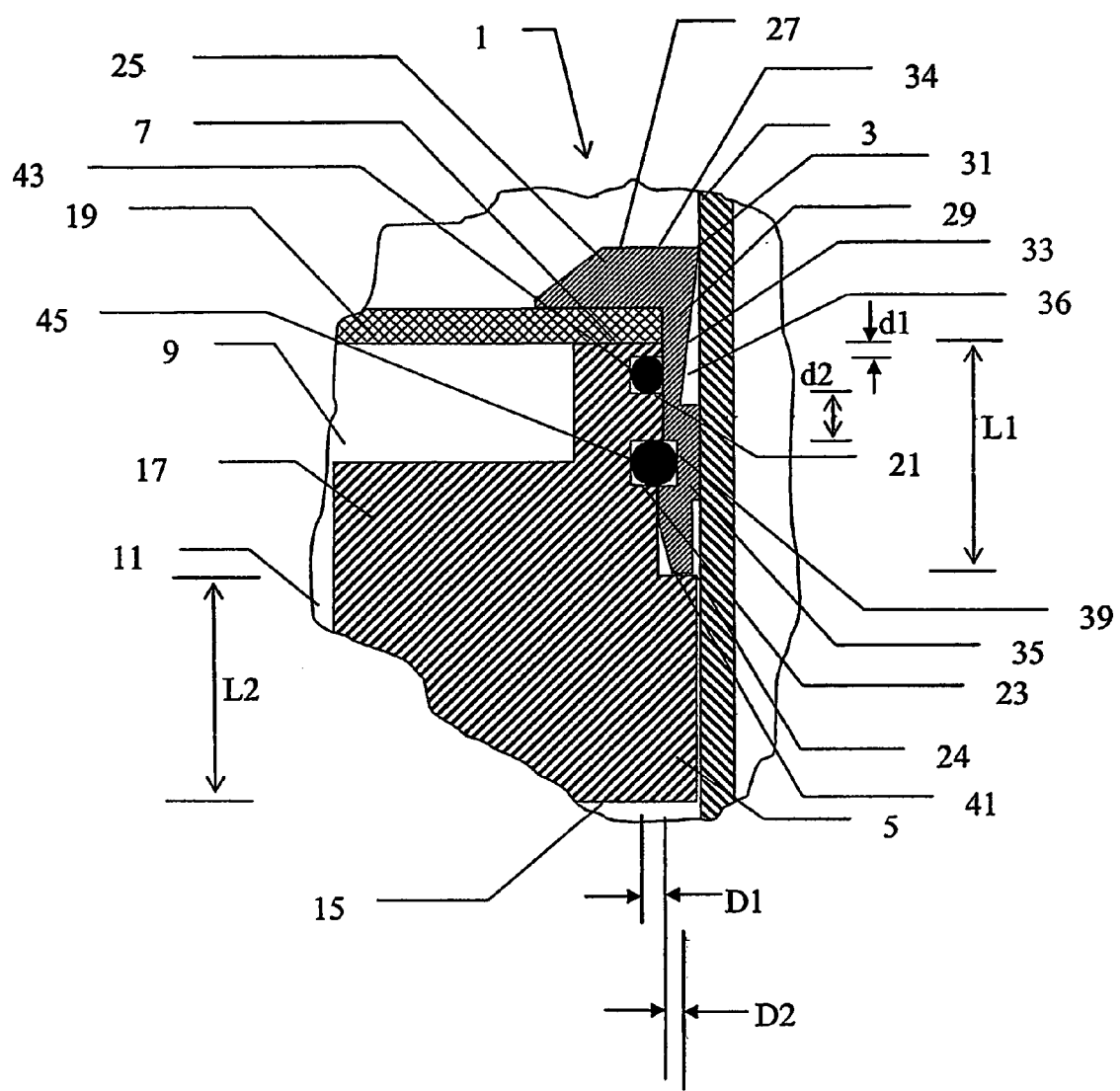
FIG. 2 shows an enlargement of a portion of the piston and scraper assembly from FIG. 1; and, FIG. 3 shows an enlargement of a portion of a second embodiment of a piston and scraper in accordance with the present invention.

FIGS. 1 and 2 show schematically a portion of a chromatography column I. Column 1 comprises a cylindrical cylinder wall 3 of internal diameter $\varnothing C$. A movable, stepped, cylindrical piston 5 closes one end of column 1. Piston 5 has a front, first face 7 which is intended to face the separation media during use and which is provided with a collecting space 9 for liquid in the column 1. A through hole 11 extends through piston 5 and connects collecting space 9 with a fluid line 13 connectable to the rear, second face 15 of piston 5. First face 7 and a first portion 17 of length L1 of piston 5 has a diameter $\varnothing 1$ which is less that the diameter $\varnothing 2$ of second face 15. The diameter $\varnothing 2$ of second face 15 and the remaining length L2 of piston 5 is sufficiently less than the internal diameter $\varnothing C$ of cylinder wall 3 so as to allow the piston to move freely up and down column 1. Collecting space 9 is covered by a liquid permeable plate 19 which allows liquid from the inside of the column 1 to flow into the collecting space 5 in the collecting space 9 but which prevents bed media from passing into the collecting space 9.

Piston 5 has spaced first and second annular grooves 21, resp. 23, provided in its cylindrical surface of diameter $\varnothing 1$. First annular groove 21 is a small distance d1 from the first face 7 and second groove 23 further away from the first face at a distance $\varnothing 2$ from first groove 21. First and second groove 23 are a depth D1 mm deep and have a square cross-section. The step 24 in the diameter of the cylindrical piston surface from diameter $\varnothing 1$ to diameter $\varnothing 2$ at distance L1 from the first face 7 of the piston is further away from the first face than d2.

A scraper 25 is attachable to the first portion 17 of piston 5 and together they form a piston and scraper assembly 26. Scraper 25 is in the form of a ring with an L-shaped cross-section. The base 27 of the L-shaped scraper 25 is intended to extend from the column wall 3 towards the centre of the column far enough that it overlaps plate 19 and thereby can retain plate 19 on piston 5, leaving a central opening of diameter $\varnothing s$. The back 29 of the L-shaped scraper 25 is intended to fit between the first portion 17 of the piston and the cylinder wall and extends in the longitudinal direction of the column from the liquid permeable plate 19 towards step 24. The length of back 29 is chosen such that back 29 does not come into contact with step 24 when correctly fitted, as if it was longer this could prevent scraper 25 being correctly fitted onto piston 5 if any foreign material was present on step 24.

Scraper 25 is intended to scrape the cylinder wall 3 and base 27 is provided with a lip 31 on its outer face 33. The diameter of lip 31 is chosen so that it is in scraping contact with cylinder wall 3 when fitted to a piston 5 inside a column 1, so lip 31 may be made of a resilient material and can have an uncompressed diameter which is greater than the internal diameter $\varnothing C$ of cylinder 3. Preferably lip 31 is arranged at a joint between the outer face 33 and the end face 34 of base 27 which faces away from piston 5. A flange 35 of an outer diameter OF such that it is in contact with cylinder wall 3 is provided at an intermediate position on back 29. Flange 35 is provided at a position on back 29 which overlaps second groove 23. The outer face 33 tapers inwards from lip 31 to the base of flange 35, leaving a gap 36 between the outer face 33 and the cylinder wall 3.

The inner face 37 of the "back" of the L-shape of scraper 25 has a diameter ØS which is a sliding fit on first portion 17 of piston 5 and is provided with a complementary sealing and locking groove 39 of depth D2 mm at a position which is opposite second annular groove 23 when scraper 25 is correctly mounted to piston 5. The inner face 37 is preferably tapered at its end 41 furthest from the base 27 in order to facilitate mounting scraper 25 onto piston 5.

First annular groove 21 contains sealing means such as a sealing ring, e.g. an O-ring 43. The dimensions of O-ring 43 are chosen such that when scraper 25 is correctly mounted then O-ring 43 prevents the passage of liquid and bed media between first portion 17 and scraper 25, thereby preventing the bed media from abrading the wall of the piston and the inner surface of the scraper. Preferably the thickness of O-ring 43 is 10%-50% greater than the depth D1.

Preferably the dimensions and elasticity of O-ring 43 are chosen so that it also pushes lip 31 against the cylinder wall 3, thereby preventing liquid and bed media from entering the gap 36 between the outer face 33 and the cylinder wall 3.

Second groove 23 contains resilient locking, sealing and biasing means such as a sealing ring, e.g. an O-ring 45. The dimensions of O-ring 45 are chosen such that when scraper 25 is correctly mounted with sealing and locking groove 39 opposite second annular groove 23 then O-ring 45 extends into sealing and locking groove 39 with sufficient force to prevent scraper 25 being pulled off piston 5 during normal use once it has been inserted into column 1. Preferably the thickness of O-ring 45 is between 10% and 100% greater than the combined depths D1+D2. O-ring 45 is also dimensioned, and its elasticity chosen, so as to seal between first portion 17 and scraper 25 as well as to push flange 35 with sealing force against cylinder wall 3, thereby preventing media entering between piston 5 and cylinder wall 3.

The scraper and piston assembly 26 can be assembled in the following way:
resilient locking, sealing and biasing means 45 is fitted into second groove 23 locking and sealing groove 39;
sealing means 43 are fitted into first groove 21;
plate 19 is positioned on first face 7;
scraper 25 is positioned with tapered end 41 against first face 7 and then pushed towards second face 15 of piston 5. As scraper 25 travels towards second face 15 its inner face 37 compresses sealing means 43 and locking, sealing and biasing means 45 until sealing and locking groove 39 on scraper 25 moves to a position opposite second groove 23. At this point resilient locking, sealing and biasing means 45 which had been compressed into second groove 23 by scraper inner face 37 expands into sealing and locking groove 39. This acts as a snap lock to hold scraper 25 onto piston 5.

Outside of the column 1, the piston and scraper assembly 26 is demountable by pulling scraper away from piston 5—as scraper 25 is not radially constrained it can expand sightly to ease the passage of its inner face 37 over locking, sealing and biasing means 43. However, once the piston and scraper assembly is fitted into column 1 then the scraper is radially constrained by the cylinder wall 3 and it more difficult to pull scraper off piston 5. Preferably the materials used in the manufacture of scraper, piston and locking, sealing and biasing means 43 and the dimensions chosen for their designs are selected so that during normal use scraper 25 cannot be removed from piston 5 when inside a column 1.

In this way, a scraper and piston assembly is provided which seals reliably, which is easy to assemble but which is secure against unwanted disassembly during use.

Figure 3:
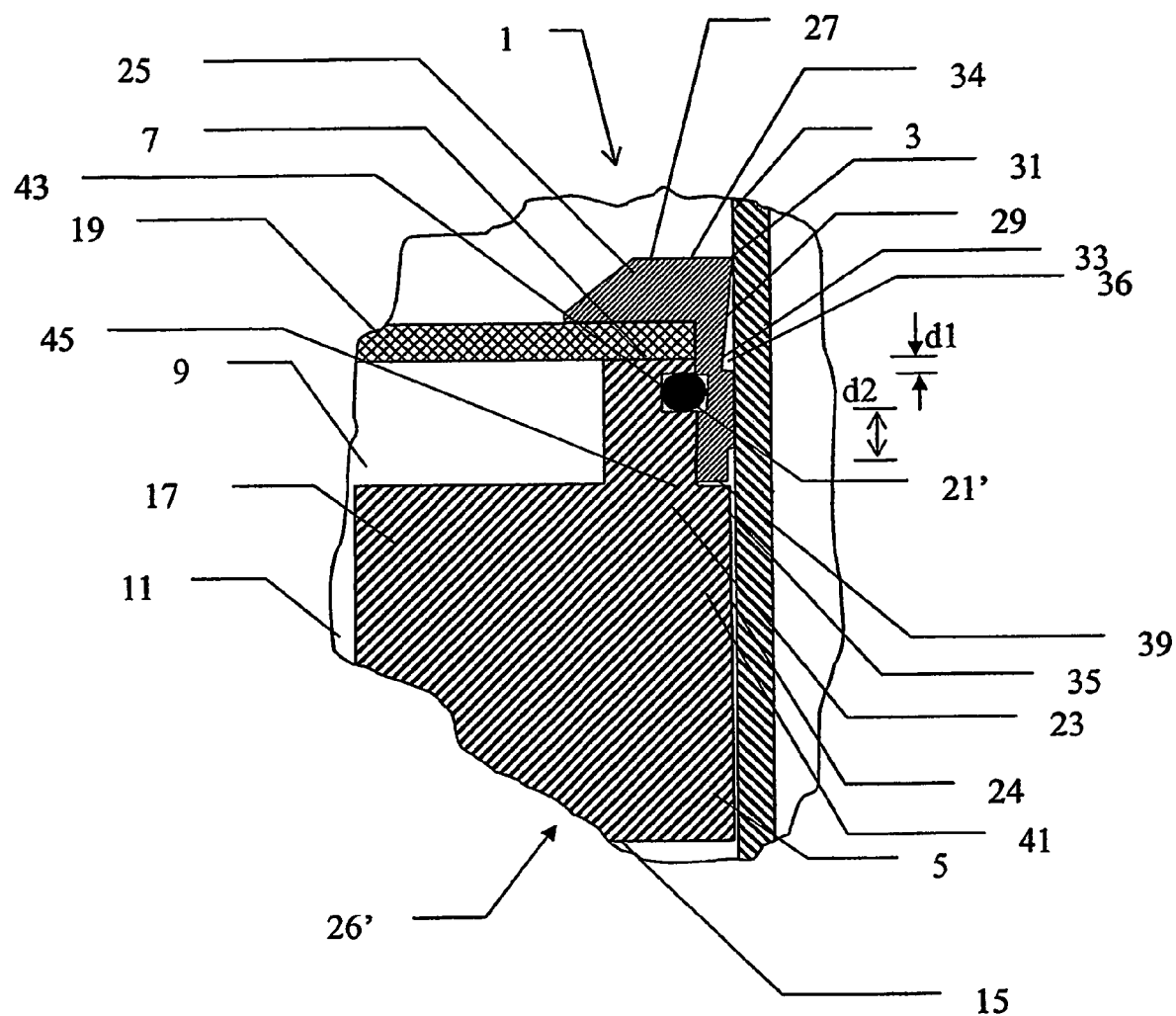

A second embodiment of a piston and scraper assembly 26' in accordance with the present invention is shown in FIG. 3. The same reference numbers are used for features which correspond to the features shown in FIGS. 1 and 2. This piston and scraper assembly 26' is provided with a single groove 23' in the piston 5 which receives a locking, sealing and biasing means 43. This embodiment does not provide such good sealing against liquid coming into contact with locking, sealing and biasing means 43 as the first embodiment of the present invention does, but is cheaper to manufacture. It is more suitable for short duration use, and may be disposed of after a short period of use, as the locking, sealing and biasing means 43 may be attacked by the liquid used in the column and wear out quickly.

Preferably scraper 25 is manufactured from a polymer material which is resistant to the fluids used during running, and cleaning of chromatography columns. Preferably the scraper material is sufficiently elastic for the scraper to be snap-fitted onto the piston. The piston may also be made from a polymer material. Suitable materials are, for example, PEHD and PTFE, optionally reinforced with fibres, e.g. glass fibres or carbon fibres.

While the embodiments of the present invention have been illustrated with examples in which the grooves have square cross-sections, other shaped cross-sections such as rectangular, semi-circular, tapered, etc are naturally also possible. The sealing rings may conceivably have cross-sections which are not round, such as X, V, oval, etc.

The above mentioned embodiments are intended only to illustrate the present invention and are not intended to limit the scope of protection claimed by the following claims.

What is claimed is:

1. A piston and scraper assembly (26, 26') for a chromatography column, comprising a piston (5) and a scraper (25) wherein said piston (5) has a front, first face (7) a cylindrical portion (17), a second, rear face (15) and a through hole (11) connecting said first face (7) to said second face (15), and is provided with an annular groove (23, 23') of depth D1 mm in the cylindrical portion (17), and wherein the scraper (25) is a ring, adapted to fit onto piston (5), having an L-shaped cross-section and having a complementary groove (39) of depth D2 mm in an inner face (37), characterised in that said annular groove (23, 23') is provided with a resilient sealing, locking and biasing means (45) which extends from said annular groove (23, 23') into said complementary groove (39) in order to retain said scraper (25) on said piston (5).

2. The piston and scraper assembly of claim 1, wherein said piston is provided with a further annular groove (21) containing a sealing means (43).

3. The piston and scraper assembly of claim 1, wherein said resilient sealing, locking and biasing means (45) is a sealing-ring with a thickness which is greater that D1+D2 mm.

4. The piston and scraper assembly of claim 2, wherein said further annular groove (21) is closer than said annular groove (23, 23') to the first, front face of piston (5).

5. The piston and scraper assembly of claim 1, wherein said scraper is made of a polymer material.

* * * * *